United States Patent
Stopp et al.

(10) Patent No.: US 6,460,398 B1
(45) Date of Patent: Oct. 8, 2002

(54) METHOD FOR DETERMINING SLIP BETWEEN TWO COMPONENT PARTS WHICH TRANSFER MOVEMENT THROUGH CONTRACTING EACH OTHER WITH FRICTION ENGAGEMENT

(75) Inventors: Ralf Stopp, Bühl; Anton Fritzer, Markdorf; Franz Bitzer, Landau, all of (DE)

(73) Assignee: LuK Lamellen und Kupplungsbau GmbH, Buhl/Baden (DE)

( * ) Notice: Subject to any disclaimer, the term of this patent is extended or adjusted under 35 U.S.C. 154(b) by 0 days.

(21) Appl. No.: 09/596,207

(22) Filed: Jun. 16, 2000

(30) Foreign Application Priority Data

Jun. 16, 1999 (DE) .......................... 199 27 401

(51) Int. Cl.$^7$ ............................................ G01M 19/00
(52) U.S. Cl. ............................................ 73/9; 474/18
(58) Field of Search .................................. 73/9

(56) References Cited

U.S. PATENT DOCUMENTS

| | | | | |
|---|---|---|---|---|
| 3,640,118 A | * | 2/1972 | Geis ............................. | 73/9 X |
| 4,295,836 A | * | 10/1981 | Kumm ........................... | 474/51 |
| 4,579,021 A | * | 4/1986 | Yamamuro et al. ............ | 74/869 |
| 4,619,629 A | * | 10/1986 | Shigematsu et al. .......... | 474/28 |
| 4,665,773 A | * | 5/1987 | Hiramatsu et al. ............. | 74/866 |
| 4,673,378 A | * | 6/1987 | Tokoro et al. ................. | 474/18 |
| 4,736,301 A | * | 4/1988 | Osanai ....................... | 364/424.1 |
| 4,824,419 A | * | 4/1989 | Kumm .......................... | 474/49 |
| 4,945,483 A | * | 7/1990 | Tokoro ....................... | 364/424.1 |
| 5,011,458 A | * | 4/1991 | Kumm .......................... | 474/49 |
| 5,038,601 A | * | 8/1991 | Renneker ....................... | 73/9 |
| 5,269,726 A | * | 12/1993 | Swanson et al. ............... | 474/28 |
| 5,515,712 A | * | 5/1996 | Yunick ........................... | 73/9 |
| 5,542,281 A | * | 8/1996 | Lee et al. ....................... | 73/9 |
| 5,932,790 A | * | 8/1999 | Hoffman et al. ................ | 73/10 |
| 6,170,452 B1 | * | 1/2001 | Wisinski ................... | 123/179.4 |

* cited by examiner

Primary Examiner—Hezron Williams
Assistant Examiner—C D Garber
(74) Attorney, Agent, or Firm—Darby & Darby

(57) ABSTRACT

In a mechanism where movement is transferred from one component to another by frictional contact and where the intensity of the frictional contact can be changed by altering the contact pressure, a method for determining the amount of slippage between the component parts uses a measurement of a value that corresponds to the power loss due to friction, also known as power dissipation, which occurs during the transfer of movement between the component parts. In this measurement, the level of power dissipation is determined in dependence on the contact pressure force, and an increase in the amount of the dissipated power that occurs when the contact pressure force decreases is interpreted as slip.

8 Claims, 3 Drawing Sheets

METHOD FOR DETERMINING SLIP BETWEEN TWO COMPONENT PARTS WHICH TRANSFER MOVEMENT THROUGH CONTRACTING EACH OTHER WITH FRICTION ENGAGEMENT

BACKGROUND OF THE INVENTION

1. Field of the Invention

The invention relates to a method for determining slip between two component parts which transfer movement through contacting each other with friction engagement in a mechanism where the intensity of the frictional contact can be changed by altering the contact pressure.

2. Description of the Related Art

FIG. 3 shows a cone pulley belt contact gearbox, such as is known for example from DE 195 44 644 A1

A fist pair of cone pulleys with cone pulleys 4, 6 is mounted on a drive shaft 2, with the cone pulley 6 being formed integral with the shaft 2 and the cone pulley 4 being connected to the shaft 2 rotationally secured but axially displaceable through axial serrations. A further pair of cone pulleys with cone pulleys 10 and 12 is mounted on a further shaft 8 which is parallel to the shaft 2, whereby the cone pulley 10 is formed integral with the shaft 8 and the cone pulley 12 is connected to the shaft rotationally secured through axial serrations but axially displaceable.

The two pairs of cone pulleys 4, 6 and 10, 12 are looped round by a contact means 14 whose links come into friction engagement with the cone faces of the cone pulleys.

To adjust the transmission ratio the distance between the cone pulleys 4, 6 and 10, 12 is mutually displaceable. For this the relevant displaceable cone pulley is loaded with pressure from each of two pressure chambers, with an inner pressure chamber 18 serving to adjust the contact pressure between the contact means 16 and the pair of cone pulleys to a preliminary pressure which is dependent on operating parameters and which can be dependent on torque for example. To relax the pressure a spring 20 is mounted in the pressure chamber 18 or in a further pressure chamber 22. The further pressure chamber 22 is preferably used in order to adjust the distance between the cone pulleys 10 and 12.

To supply the pressure chambers with pressure there is a hydraulic medium pump 24 which supplies pressure controllable through the control valves 26 to the pressure chambers 18 which are biased with contact pressure, and supplies pressure to the adjustment chambers 22 through control valves 28.

Hydraulic medium which serves to cool the friction faces and for lubrication is introduced into the space between the cone pulleys for example through openings 30 in the shafts or in another suitable manner. The overflowing hydraulic medium is collected in a funnel 32 which leads into a return container 34 from which the hydraulic pump 24 sucks in the hydraulic medium.

The pressure chambers 18 of the two pairs of cone pulleys can like the adjustment chambers 22 of the two pairs of cone pulleys each be controlled through a common control valve.

The function and construction of the cone pulley belt contact gearbox described are known per se so that detailed explanation is not provided.

One problem which exists with cone pulley belt contact gearboxes of the kind mentioned is that the contact pressure between the friction faces of the cone pulley and the contact means should not be unnecessarily great since this leads on the one hand to an unnecessarily high energy consumption by the pump 24 and on the other leads to an unnecessarily high strain on the cone pulley belt contact gearbox overall. If the contact pressure is too low then there is the danger that the contact means slip on the cone pulleys which leads to a significantly increased wear. The measurement of the slip is a problem when not the speed of the contact means itself, but the active radii of the pairs of cone pulleys and their speeds are measured. The speeds of the pairs of cone pulleys are not a reliable measure for determining the slip. Since the slip can only be measured with comparative inaccuracy, and a state of slip is however dangerous for the durability of the gearbox, it is general to drive with a certain reserve contact pressure, i.e. with a contact pressure which is too high in itself.

OBJECT OF THE INVENTION

The object of the invention is to provide a method for determining the slip between the contact means and the pairs of friction discs which leads with simple implementation to excellent results.

SUMMARY OF THE INVENTION

To achieve the foregoing objective, the method according to the invention uses a measurement of a value that corresponds to the power loss due to friction, also known as power dissipation, which occurs during the transfer of movement between the component parts. In this measurement, the power dissipation is determined in dependence on the contact pressure force, and a rise in the amount of power that is dissipated when the contact pressure force decreases is interpreted as slip.

The invention is based on the knowledge that the power dissipation due to friction which occurs between the contact means and the friction faces of the cone pulleys is comparatively slight substantially independent of the torque that is being transferred, provided no slip is present. As soon as slip occurs when the contact pressure drops, the level of power dissipation rapidly increases so that when the power dissipation or a value which corresponds to same, is measured the presence of slip is reliably detected.

The method according to the invention is suitable for all applications where movement is transferred through friction contact, such as toroidal gears, CVT gearboxes in general or other transmission systems.

BRIEF DESCRIPTION OF THE DRAWINGS

The invention will now be explained by way of example with reference to the accompanying drawings in which.

DETAILED DESCRIPTION OF PREFERRED EMBODIMENTS

Figure 1:
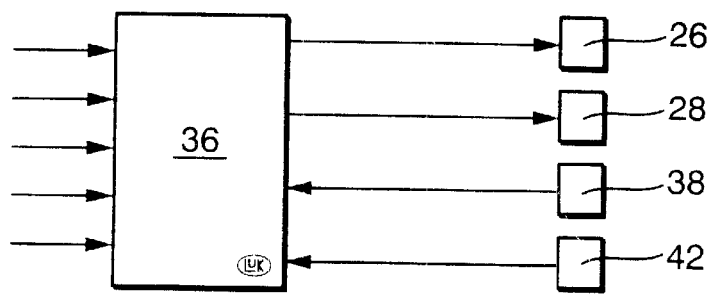
FIG. 1 shows a block circuit diagram of a control circuit for the gearbox of FIG. 3.
Figure 3:
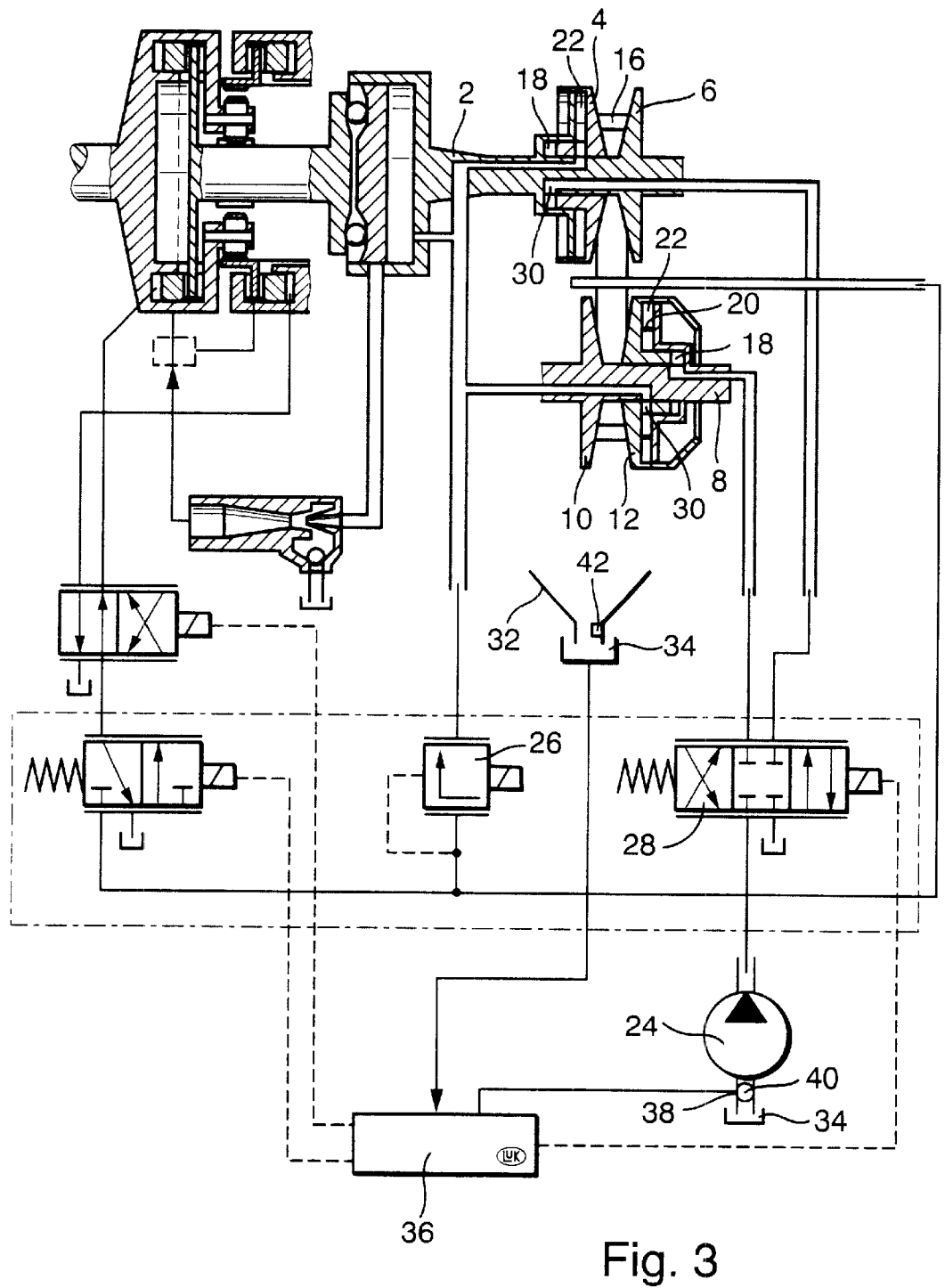
FIG. 3 shows the cone pulley belt contact gearbox already explained.

According to FIG. 1 the outputs of a control device 36 provided with a micro processor and associated memory devices are connected to the or each control valve 26 for controlling the contact pressure and to the or each control valve 28 for controlling the adjustment pressure. A through-flow measuring apparatus 38 which is mounted in the suction pipe 40 of the pump 24 (FIG. 3) is connected to the input of the control device 36. A temperature sensor 42 in the funnel (FIG. 3) is connected to a further input of the control device 36 whose other inputs are connected in known way to sensors from which signals are derived for controlling the transmission ratio and contact pressure.

So long as the gearbox runs free of slip the hydraulic medium returning to the funnel 32 remains comparatively cool. If as a result of insufficient contact pressure slip occurs, then a comparatively high level of power dissipation occurs at the friction faces of the cone pulleys and this manifests itself through the heating up of the hydraulic medium flowing back into the funnel 32, which is detected by the temperature sensor 42. Instead of the oil flowing back into the funnel other oil on other operating areas of the gearbox can also be monitored with regard to temperature. Instead of the funnel it is also possible to use a different element in a further embodiment.

Figure 2:
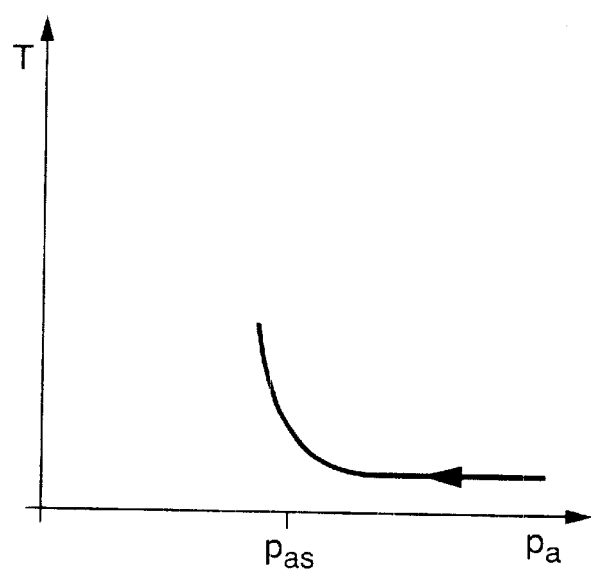
FIG. 2 shows a graph for explaining the method according to the invention.

FIG. 2 shows an example of a measuring graph. $P_a$ indicates the contact pressure controlled through the control valve 26 in the pressure chamber 18. T indicates the temperature. When the contact pressure $p_a$ drops from a pressure which is sufficient for a slip-free operation, then with a pressure $p_{as}$ a sudden rise in temperature appears on the temperature sensor 42 which indicates the presence of slip. The contact pressure $p_a$ can now be kept by the control device 36 at a value which lies according to FIG. 2 slightly to the right of $p_{as}$, i.e. at which a slip free operation is guaranteed.

Using the control device 36 it is now possible to control the depicted drop in pressure routinely in the event of different torques acting on the drive shaft 2, which are known from operating parameters of the drive motor (not shown), and speeds according to FIG. 2 are implemented each time so that the pressure $p_{as1}$, beneath which slip sets in, in dependence on the torque and/or the speed and/or the gear transmission ratio can be stored in a characteristic field and by means of the control device 36 the control valve 26 can be controlled correspondingly so that a slip-free operation prevails but no unnecessarily high contact pressure is present. It is evident that the knowledge of the slip pressure $p_{as}$ can also be used to produce in certain operating states a slipping operation when this is desired.

The two pairs of cone pulleys can be checked separately from each other for slipping operation, or with the method depicted in FIG. 2 can be measured through a purposeful lowering and raising of the contact pressure and then controlled accordingly when the oil flowing back from the pairs of cone pulleys is collected up separately and measured.

It is evident that the measuring process described can be modified in many ways. By way of example the through flow of the hydraulic medium which cools the or each pair of cone pulleys can be measured by means of one or more through-flow measuring instruments 38. By way of further temperature sensors it is possible to measure the temperature of the hydraulic medium upstream of the relevant pair of cone pulleys so that from the temperature difference between the hydraulic medium flowing into the pair of cone pulleys and the temperature of the hydraulic medium flowing back, the through-flow speed and the specific heat of the hydraulic medium it is possible to reach a final conclusion on the amount of power being dissipated through friction.

Alternatively by means of contactlessly operating temperature sensors, for example by means of radiation temperature sensors, it is possible to determine directly the temperature of the friction surfaces, whereby these temperatures change in a similar way to that described in FIG. 2.

A great advantage of the method according to the invention is that it can be used completely independently of the state of wear of the cone pulley belt contact gearbox or the state of the hydraulic medium since the jump in temperature which appears when slip sets in calibrates the method in a certain way itself.

It is evident that the method can also be used with cone pulley belt contact gearboxes whose cone pulleys are each only pressed against the contact means through one pressure chamber or electrically or mechanically.

Figure 4:
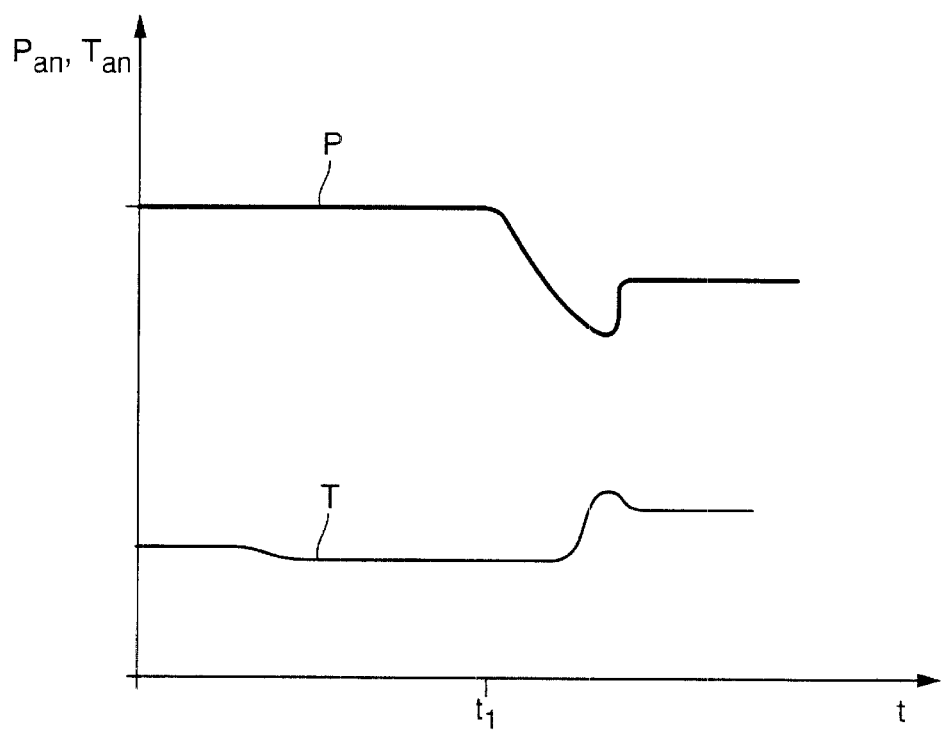
FIG. 4, shows a diagram.

FIG. 4 shows a diagram in which the temperature T and contact pressure P of the cone pulleys are shown as a function of the time t. AT time point $t_1$ a method is started for determining the slip limit and the contact pressure is reduced. Slip is thereby set and the temperature rises. The contact pressure P is then raised again and the temperature T swings to a higher level again.

The patent claims filed with the application are proposed wordings without prejudice for obtaining wider patent protection. The applicant retains the right to claim further features disclosed up until now only in the description and/or drawings.

References used in the oub-claims refer to further designs of the subject of the main claim through the features of each relevant sub-claim; they are not to be regarded as dispensing with obtaining an independent subject protection for the features of the sub-claims referred to.

The subjects of these sub-claims however also form independent inventions which have a design independent of the subjects of the preceding claims.

The invention is also not restricted to the embodiments of the description. Rather numerous amendments and modifications are possible within the scope of the invention, particularly those variations, elements and combinations and/or materials which are inventive for example through combination or modification of individual features or elements or process steps contained in the drawings and described in connection with the general description and embodiments and claims and which through combinable features lead to a new subject or to new process steps or sequence of process steps insofar as these refer to manufacturing, test and work processes.

What is claimed is:

1. Method for determining slip between two component parts which transfer movement through contacting one another with friction engagement in a mechanism where the intensity of the friction contact can be changed by altering the contact pressure force which acts between the component parts, wherein a value corresponding to an amount of power dissipated through friction which arises during the transfer of movement between the component parts is measured in dependence on the contact pressure force and a rise in said amount of power when the contact pressure force decreases is evaluated as slip, wherein a temperature of at least one of the component parts is measured, wherein a temperature of a flow of fluid for at least one of lubricating and cooling at least one of the component parts is measured downstream of the component part, wherein a rate at which heat is absorbed by the flow of fluid during its flow along the at least one component part is measured.

2. Method according to claim 1, wherein the transfer of movement in said mechanism takes place with a variable transmission ratio.

3. Method according to claim 1, wherein the motion transferring component parts are a pair of cone pulleys and the contact means is a cone pulley belt contact gearbox.

4. Method according to claim 3, wherein through varying the contact pressure between at least one of the cone pulleys with different speeds, different torque, transmission ratios and temperatures a characteristic field is recorded which represents the contact pressure forces required for the defined slip in dependence on at least one of the speed, torque, transmission ratio and temperature, and the contact pressure between the cone pulleys is set according to the characteristic field.

5. Method for determining slip between two component parts which transfer movement through contacting one another with friction engagement in a mechanism where the intensity of the friction contact can be changed by altering the contact pressure force which acts between the component parts, wherein a value corresponding to an amount of power dissipated through friction which arises during the transfer of movement between the component parts is measured in dependence on the contact pressure force and a rise in said amount of power when the contact pressure force decreases is evaluated as slip, wherein a temperature of at least one of the component parts is measured, wherein with at least approximately constant conditions by changing the contact pressure force a slip limit is determined and the contact pressure force is then set so that no slip occurs or a predetermined slip boundary value is not exceeded, wherein the motion transferring component parts are a pair of cone pulleys, wherein through varying the contact pressure between at least one of the cone pulleys with different speeds, different torque, transmission ratios and temperatures a characteristic field is recorded which represents the contact pressure forces required for the defined slip in dependence on at least one of the speed, torque, transmission ratio and temperature, and the contact pressure between the cone pulleys is set according to the characteristic field.

6. Method according to claim 5, wherein a temperature of fluid for at least one of lubricating and cooling at least one of the component parts is measured downstream, of the component part.

7. Method according to claim 5, wherein the at least approximately constant condition is at least one of transferred force, speed and transmission ratio.

8. Method according to claim 5, wherein the transfer of movement in said mechanism takes place with a variable transmission ratio.

* * * * *

UNITED STATES PATENT AND TRADEMARK OFFICE
CERTIFICATE OF CORRECTION

PATENT NO. : 6,460,398 B1
DATED : October 8, 2002
INVENTOR(S) : Ralf Stopp et al.

It is certified that error appears in the above-identified patent and that said Letters Patent is hereby corrected as shown below:

<u>Title page,</u>
Item [73], Assignee, delete "LuK Lamellen und Kupplungsbau GmbH, Buhl/Baden" and substitute -- Luk Lamellen und Kupplungsbau Beteiligungs KG, Buhl --.

Signed and Sealed this

Twentieth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,460,398 B1  Page 1 of 1
APPLICATION NO. : 09/596207
DATED : October 8, 2002
INVENTOR(S) : Ralf Stopp et al.

It is certified that error appears in the above-identified patent and that said Letters Patent is hereby corrected as shown below:

<u>Title page,</u>
Item [73], Assignee, delete "LuK Lamellen und Kupplungsbau GmbH, Buhl/Baden" and substitute -- LuK Lamellen und Kupplungsbau Beteiligungs KG, Buhl --.

This certificate supersedes Certificate of Correction issued May 20, 2003.

Signed and Sealed this

Second Day of October, 2007

JON W. DUDAS
*Director of the United States Patent and Trademark Office*